United States Patent
Shimizu et al.

(10) Patent No.: US 10,118,888 B2
(45) Date of Patent: Nov. 6, 2018

(54) METHOD FOR ISOMERIZING BIS(AMINOMETHYL) CYCLOHEXANE

(71) Applicant: Mitsubishi Gas Chemical Company, Inc., Chiyoda-ku (JP)

(72) Inventors: Yuko Shimizu, Chiyoda-ku (JP); Yoshiaki Yamamoto, Katsushika-ku (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 15/556,329

(22) PCT Filed: Feb. 25, 2016

(86) PCT No.: PCT/JP2016/055613
§ 371 (c)(1),
(2) Date: Sep. 7, 2017

(87) PCT Pub. No.: WO2016/143539
PCT Pub. Date: Sep. 15, 2016

(65) Prior Publication Data
US 2018/0044279 A1    Feb. 15, 2018

(30) Foreign Application Priority Data

Mar. 9, 2015    (JP) .................................. 2015-045796

(51) Int. Cl.
| C07C 209/68 | (2006.01) |
| C07C 211/18 | (2006.01) |
| C07B 61/00  | (2006.01) |

(52) U.S. Cl.
CPC .......... C07C 209/68 (2013.01); C07C 211/18 (2013.01); C07B 61/00 (2013.01); C07B 2200/07 (2013.01); C07C 2601/14 (2017.05)

(58) Field of Classification Search
CPC . C07C 209/68; C07C 211/18; C07C 2601/14; C07B 61/00; C07B 2200/07
See application file for complete search history.

(56) References Cited

U.S. PATENT DOCUMENTS

| 4,086,276 A * | 4/1978 | Butte, Jr. .............. C07C 211/18 564/444 |
| 5,969,187 A | 10/1999 | Okawa et al. |
| 2010/0216905 A1 | 8/2010 | Kuwamura et al. |
| 2017/0204049 A1 | 7/2017 | Yamamoto et al. |

FOREIGN PATENT DOCUMENTS

| JP | 50-126638 A | 10/1975 |
| JP | 53-130637 A | 11/1978 |
| JP | 54-041804 A | 4/1979 |
| JP | 62-003144 B2 | 1/1987 |
| JP | 10-259167 A | 9/1998 |
| JP | 10-306066 A | 11/1998 |
| JP | 10-330329 A | 12/1998 |
| JP | 11-335335 A | 12/1999 |
| JP | 4117424 B2 | 7/2008 |
| JP | 5448987 B2 | 3/2014 |
| WO | 2009/051114 A1 | 4/2009 |
| WO | 2015/041261 A1 | 3/2015 |

OTHER PUBLICATIONS

Waddel et al., "Conducting moisture sensitive reactions under mechanochemical conditions," Tetrahedron Letters, 53(34), 2012, pp. 4510-4513 (Year: 2012).*
Prince, Frank R., et al., "Cis/Trans Copolyamides of 1,4-Bisaminomethylcyolohexane", Journal of Polymer Science (1972), vol. 10, Part A-1, pp. 465-470.
Kobunshi Ronbunshu, Japanese Journal of Polymer Science and Technology (May 1979), vol. 36, No. 5, pp. 305-310.
International Search Report dated May 24, 2016 in PCT/JP2016/055613, filed Feb. 25, 2016.

* cited by examiner

*Primary Examiner* — Pancham Bakshi
*Assistant Examiner* — Mark R Luderer
(74) *Attorney, Agent, or Firm* — Oblon, McClelland, Maier & Neustadt, L.L.P.

(57) ABSTRACT

A method for isomerizing a bis(aminomethyl)cyclohexane, including isomerizing a bis(aminomethyl)cyclohexane while introducing an inert gas in a reaction solution containing
  a bis(aminomethyl)cyclohexane,
  at least one selected from the group consisting of an alkali metal, an alkali metal-containing compound, an alkaline earth metal and an alkaline earth metal-containing compound, and
  a benzylamine compound.

20 Claims, 1 Drawing Sheet

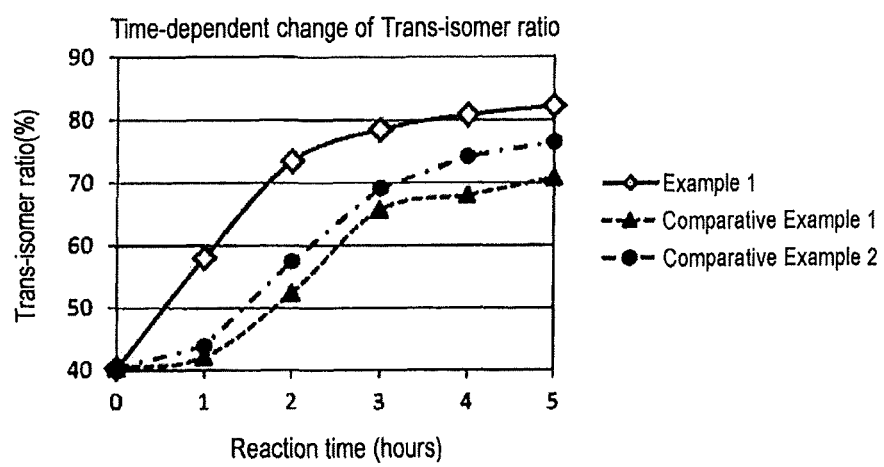

METHOD FOR ISOMERIZING BIS(AMINOMETHYL) CYCLOHEXANE

TECHNICAL FIELD

The present invention relates to a method for isomerizing a bis(aminomethyl)cyclohexane.

BACKGROUND ART

A bis(aminomethyl)cyclohexane is an industrially important compound to be used as a starting material for e.g., epoxy hardeners, polyamides and polyurethanes. A bis(aminomethyl)cyclohexane has two isomers, i.e., a cis-isomer and a trans-isomer, derived from a cyclohexane ring. It is known that the physical properties of a polymer obtained by using a bis(aminomethyl)cyclohexane greatly vary depending upon the ratio of isomers, i.e., the ratio of a cis-isomer and a trans-isomer.

For example, it is known that for a polyamide obtained by using 1,4-bis(aminomethyl)cyclohexane, as the content of a trans-isomer increases, the melting point increases, with the result that the heat resistance increases (Non Patent Literature 1). It is also known that a polyurethane obtained by using 1,4-bis isocyanatomethyl cyclohexane derived from 1,4-bis(aminomethyl)cyclohexane is improved in physical properties required for various applications as the content of a trans-isomer increases (Patent Literature 1).

It is further reported that a polyamide, which is obtained by using 1,3-bis(aminomethyl)cyclohexane, having a high cis-isomer content has high crystallinity; whereas a polyamide having a high trans-isomer content is amorphous (Non Patent Literature 2).

For these reasons, it is extremely important to control the isomer ratio of a bis(aminomethyl)cyclohexane.

Bis(aminomethyl)cyclohexane is produced by a method known in the art. To describe more specifically, a bis(aminomethyl)cyclohexane can be obtained by hydrogenating an aromatic dinitrile in the presence of a catalyst to synthesize a xylylenediamine and nuclear-hydrogenating the xylylenediamine obtained in the presence of a catalyst.

A large number of methods are known in the art for producing a xylylenediamine from an aromatic dinitrile by hydrogenation; for example, a method using a Raney catalyst such a Raney nickel or Raney cobalt is reported (Patent Literature 2).

A large number of methods are also known in the art for producing a bis(aminomethyl)cyclohexane by nuclear hydrogenation of a xylylenediamine. In the nuclear hydrogenation reaction of a xylylenediamine, a cis-isomer is more easily produced than a trans-isomer. Thus, it is generally difficult to selectively synthesize a trans-isomer.
For example, a method using a catalyst having ruthenium immobilized to a carrier is reported (Patent Literature 3); however the proportion of a trans-isomer of a bis(aminomethyl)cyclohexane synthesized by this method is generally 50% or less.

Up to present, an isomerization reaction for obtaining 1,4-bis(aminomethyl)cyclohexane having a high content of a trans-isomer has been proposed. For example, a method for obtaining trans-1,4-bis(aminomethyl)cyclohexane by isomerizing 1,4-bis(aminomethyl)cyclohexane in the presence of a noble metal catalyst such as platinum or ruthenium is reported (Patent Literatures 4-6).

Another method for obtaining trans-1,4-bis(aminomethyl) cyclohexane is reported, in which 1,4-bis(aminomethyl) cyclohexane is derivatized into an aldimine compound and then isomerization is carried out and the aldimine compound is decomposed (Patent Literature 7).

Also, as a method for obtaining 1,4-bis(aminomethyl) cyclohexane having a high content of a trans-isomer, a method of obtaining 1,4-bis(aminomethyl)cyclohexane from starting terephthalic acid via a cyclohexane dicarboxylic acid, is reported (Patent Literature 8).

Furthermore, a method of isomerizing 1,4-bis(aminomethyl)cyclohexane by blending it with a benzylamine compound and an alkali metal, an alkali metal hydride or an alkali metal amide is reported (Patent Literature 9). In this method, it is possible to isomerize a bis(aminomethyl) cyclohexane without passing through a complicated multi-stage process.

CITATION LIST

Patent Literatures

Patent Literature 1: International Publication No. WO2009/051114
Patent Literature 2: Japanese Patent Laid-Open No. S54-41804
Patent Literature 3: Japanese Patent Laid-Open No. S50-126638
Patent Literature 4: Japanese Patent Laid-Open No. H10-259167
Patent Literature 5: Japanese Patent Laid-Open No. H10-306066
Patent Literature 6: Japanese Patent No. 4117424
Patent Literature 7: Japanese Patent Laid-Open No. H10-330329
Patent Literature 8: Japanese Patent No. 5448987
Patent Literature 9: Japanese Patent Publication No. 562-3144

Non Patent Literatures

Non Patent Literature 1: J. Polym. Sci. PartA-1, 10, 465 (1972)
Non Patent Literature 2: Kobunshi Ronbunshu, Vol. 36 No. 5 pp. 305-310 (1979)

SUMMARY OF INVENTION

Technical Problem

However, in the methods described in Patent Literatures 4 to 6, in order to obtain 1,4-bis(aminomethyl)cyclohexane in a high yield, it is necessary to carry out isomerization in liquid ammonia. Because of this, there is a drawback of a high-pressure reaction. If liquid ammonia is not used, a high recovery rate cannot be obtained.

In the method described in Patent Literature 7, a trans-isomer can be obtained in an extremely high proportion of 99%. However, three steps must be carried out for isomerization and an extremely complicated step is required for recycling an aldehyde for use in derivatization. Because of this, this method is industrially not easily carried out.

In the method described in Patent Literature 8, in order to increase the content of a trans-isomer, the trans-isomer is separated from a precursor, 1,4-dicyanocyclohexane, by crystallization, and the remaining cis-isomer is isomerized and recycled. However, this method requires an extremely long step and thus industrially unfavorable.

In the method described in Patent Literature 9, in order to obtain a trans-isomer in a high proportion, a large amount of a catalyst is used or a high temperature condition is required. This method is inefficient.

The present invention was attained in view of the above problems. An object of the invention is to easily and efficiently obtain a bis(aminomethyl)cyclohexane having a high isomer content through an isomerization reaction of an industrially important compound, a bis(aminomethyl)cyclohexane, without passing through a high-temperature and high-pressure reaction or a complicated multi-stage process.

Solution to Problem

The present inventors conducted intensive studies with a view to solving the aforementioned problems. As a result, they found that the isomerization reaction of a bis(aminomethyl)cyclohexane can be promoted by isomerizing the bis(aminomethyl)cyclohexane in a reaction solution containing at least one selected from the group consisting of an alkali metal, an alkali metal-containing compound, an alkaline earth metal and an alkaline earth metal-containing compound and a benzylamine compound, while introducing an inert gas. Based on the finding, the present invention was accomplished.

More specifically, the present invention is as follows.

[1]
A method for isomerizing a bis(aminomethyl)cyclohexane, comprising isomerizing a bis(aminomethyl)cyclohexane while introducing an inert gas in a reaction solution containing
  a bis(aminomethyl)cyclohexane,
  at least one selected from the group consisting of an alkali metal, an alkali metal-containing compound, an alkaline earth metal and an alkaline earth metal-containing compound, and
  a benzylamine compound.

[2]
The method for isomerizing a bis(aminomethyl)cyclohexane according to above [1], wherein the inert gas is at least one selected from the group consisting of helium, argon and nitrogen.

[3]
The method for isomerizing a bis(aminomethyl)cyclohexane according to above [1] or [2], wherein the benzylamine compound is at least one selected from the group consisting of benzylamine, 3-methylbenzylamine, 4-methylbenzylamine, dibenzylamine, meta-xylylenediamine and para-xylylenediamine.

[4]
The method for isomerizing a bis(aminomethyl)cyclohexane according to any of above [1] to [3], wherein the benzylamine compound is 4-methylbenzylamine.

[5]
The method for isomerizing a bis(aminomethyl)cyclohexane according to any of above [1] to [4], wherein the alkali metal-containing compound contains sodium amide.

[6]
The method for isomerizing a bis(aminomethyl)cyclohexane according to any of above [1] to [5], wherein an isomerization reaction temperature is 100 to 140° C.

[7]
The method for isomerizing a bis(aminomethyl)cyclohexane according to any of above [1] to [6], wherein a method for introducing the inert gas is bubbling.

[8]
The method for isomerizing a bis(aminomethyl)cyclohexane according to any of above [1] to [7], wherein the bis(aminomethyl)cyclohexane is 1,4-bis(aminomethyl)cyclohexane.

[9]
The method for isomerizing a bis(aminomethyl)cyclohexane according to any of above [1] to [7], wherein the bis(aminomethyl)cyclohexane is 1,3-bis(aminomethyl)cyclohexane.

[10]
The method for isomerizing a bis(aminomethyl)cyclohexane according to above [8], wherein the 1,4-bis(aminomethyl)cyclohexane is obtained in a trans-isomer content of 77% or more.

[11]
The method for isomerizing a bis(aminomethyl)cyclohexane according to above [9], wherein the 1,3-bis(aminomethyl)cyclohexane is obtained in a cis-isomer content of 80% or more.

Advantageous Effects of Invention

Owing to the present invention, it is possible to provide a method for isomerizing a bis(aminomethyl)cyclohexane simply and efficiently compared to a technique in the prior art.

BRIEF DESCRIPTION OF DRAWINGS

The FIGURE shows time-dependent changes of the trans-isomer proportion in Example 1, Comparative Example 1 and Comparative Example 2.

DESCRIPTION OF EMBODIMENT

Now, an embodiment (hereinafter referred to as "the embodiment") will be more specifically described below; however, the present invention is not limited to this and may be modified in various ways without departing from the scope of the invention.

[Method for Isomerizing a Bis(Aminomethyl)Cyclohexane]

The present invention relates to a method for isomerizing a bis(aminomethyl)cyclohexane, comprising isomerizing a bis(aminomethyl)cyclohexane while introducing an inert gas in a reaction solution containing
  a bis(aminomethyl)cyclohexane,
  at least one selected from the group consisting of an alkali metal, an alkali metal-containing compound, an alkaline earth metal and an alkaline earth metal-containing compound, and
  a benzylamine compound.

In the method for isomerizing a bis(aminomethyl)cyclohexane of the embodiment, since an isomerization reaction is promoted by carrying out the reaction while introducing an inert gas, the isomerization reaction of a bis(aminomethyl)cyclohexane can be more efficiently carried out than methods according to the prior art.

Examples of the bis(aminomethyl)cyclohexane include, but are not particularly limited to, 1,3-bis(aminomethyl)cyclohexane and 1,4-bis(aminomethyl)cyclohexane. Of them, in order for the effect of the present invention to become further more prominent, 1,4-bis(aminomethyl)cyclohexane is preferable. As the 1,3-bis(aminomethyl)cyclohexane, a trans-isomer is preferable. As the 1,4-bis(aminomethyl)cyclohexane, a cis-isomer is preferable. Note that, the 1,3-bis(aminomethyl)cyclohexane and 1,4-bis(aminomethyl)cyclohexane each may be a mixture of a trans-isomer and a cis-isomer.

A method for producing a cis-isomer and a trans-isomer of a bis(aminomethyl)cyclohexane or a mixture thereof is not particularly limited; however, e.g., a method of nuclear-hydrogenating para-xylylenediamine or meta-xylylenediamine in the presence of a noble metal catalyst such as ruthenium, palladium, rhodium or platinum is mentioned.

The term "to isomerize" refers to transforming a trans-isomer of a bis(aminomethyl)cyclohexane into a cis-isomer thereof or transforming a cis-isomer of a bis(aminomethyl)cyclohexane into a trans-isomer thereof, more specifically, transforming a trans-isomer of 1,3-bis(aminomethyl)cyclohexane into a cis-isomer thereof or transforming a cis-isomer of 1,4-bis(aminomethyl)cyclohexane into a trans-isomer thereof.

In the isomerization method of the embodiment, for example, if a mixture of a cis-isomer and a trans-isomer of 1,4-bis(aminomethyl)cyclohexane is subjected to an isomerization reaction, the cis-isomer of 1,4-bis(aminomethyl)cyclohexane is transformed into the trans-isomer of 1,4-bis(aminomethyl)cyclohexane by isomerization. Alternatively, if a mixture of a cis-isomer and a trans-isomer of 1,3-bis(aminomethyl)cyclohexane is subjected to an isomerization reaction, the trans-isomer of 1,3-bis(aminomethyl)cyclohexane is transformed into the cis-isomer of 1,3-bis(aminomethyl)cyclohexane by isomerization.

As the inert gas, although it is not particularly limited, an inert gas which does not inhibit an isomerization reaction can be used. Examples of the inert gas include rare gases such as helium, neon, argon, krypton, xenon and radon; hydrocarbons such as methane and ethane; and nitrogen. In view of availability, preferably helium, argon and nitrogen are used. An isomerization reaction can be more efficiently promoted by carrying out the isomerization reaction while introducing an inert gas in a reaction solution.

The method for introducing an inert gas in a reaction solution is not particularly limited. For example, injection (bubbling) of an inert gas in a reaction solution may be mentioned.

An inert gas may be continuously or intermittently introduced in a reaction solution. In the case of intermittent introduction, the introduction interval and introduction period of time are not particularly limited as long as the effect of the invention is not undermined. In order for the effect of the present invention to become further more prominent, it is preferable that an inert gas is continuously introduced.

The flow rate of an inert gas is not particularly limited because the flow rate varies depending upon e.g., the production scale, diameter of a reactor, inert gas introduction mode, amounts of individual components to be used and reaction conditions. Usually, the larger the flow rate, the easier the effect of promoting the reaction tends to be obtained; however, a large amount of an inert gas is required. The flow rate of an inert gas per bis(aminomethyl)cyclohexane (100 g) is preferably 10 mL/minute or more, more preferably 20 mL/minute or more and further preferably 50 to 500 mL/minute.

When an inert gas is introduced, the reaction solution is preferably stirred. If stirred, the inert gas is satisfactorily dispersed and the effect of introducing the inert gas tends to be sufficiently obtained.

The isomerization reaction temperature, although it is not particularly limited, is preferably 10 to 200° C., more preferably 80 to 150° C., further preferably 100 to 140° C. and particularly preferably 100 to 124° C. If the isomerization reaction temperature is 10° C. or more, the isomerization reaction tends to further efficiently and successfully proceed. In contrast, if the isomerization reaction temperature is 200° C. or less, a side reaction such as a decomposition reaction and a polymerization reaction, can be suppressed and production of by-products such as a low-boiling product and a high-boiling product can be reduced, with the result that the recovery rate of a bis(aminomethyl)cyclohexane tends to be further improved. Particularly, if the isomerization reaction temperature is 100 to 140° C., satisfactory yield and reaction rate tend to be successfully obtained.

The isomerization reaction time, which varies depending upon e.g., the amount of individual components to be used, reaction conditions and the desired isomer composition, is preferably 0.50 to 6.0 hours and more preferably 1.0 to 5.0 hours.

The isomerization reaction can be carried out both in the presence and absence of a solvent. The solvent to be used in the reaction is not particularly limited; however, e.g., an inert solvent can be mentioned. Specific examples include aromatic solvents such as benzene, toluene and xylene; ether solvents such as diethyl ether and tetrahydrofuran; and hydrocarbon solvents such as hexane and heptane. Of them, in order to more efficiently promote an isomerization reaction, a solvent having a boiling point equal to or lower than the isomerization reaction temperature is preferably used.

As the isomerization reaction atmosphere, although it is not particularly limited, for example, an atmosphere not containing air or active hydrogen such as water or an alcohol, is preferable. If so, the reaction efficiency tends to be further improved. Particularly, in view of reaction efficiency, the water content of the reaction system is preferably controlled to be 1000 ppm or less.

Examples of the benzylamine compound to be used in the isomerization reaction of the embodiment include, but are not particularly limited to, mono-benzylamine compounds such as benzylamine, 2-methylbenzylamine, 3-methylbenzylamine and 4-methylbenzylamine; secondary benzylamine compounds such as dibenzylamine and N-methylbenzylamine; and compounds having two aminomethyl groups such as meta-xylylenediamine and para-xylylenediamine. Of these, in view of reaction efficiency, it is preferable to use at least one selected from the group consisting of benzylamine, 3-methylbenzylamine, 4-methylbenzylamine, dibenzylamine, meta-xylylenediamine and para-xylylenediamine. These compounds may be used singly or in combination of two or more.

The amount of the benzylamine compound used herein relative to one mole of a bis(aminomethyl)cyclohexane is preferably 0.001 to 0.10 mol equivalents and more preferably 0.002 to 0.05 mol equivalents. If the amount of the benzylamine compound used herein falls within the above range, the isomerization reaction smoothly proceeds and a side reaction such as a polymerization reaction between bis(aminomethyl)cyclohexane molecules can be suppressed. As a result, the yield of a desired isomer is further improved and the catalyst cost tends to be successfully kept down.

In the isomerization reaction of the embodiment, at least one selected from the group consisting of an alkali metal, an alkali metal-containing compound, an alkaline earth metal and an alkaline earth metal-containing compound is used. If such a compound is used, the isomerization reaction can more efficiently proceed. These compounds may be used singly or in combination of two or more.

Examples of the alkali metal include, but are not particularly limited to, metallic sodium, metallic potassium and metallic lithium.

Examples of the alkali metal-containing compound include, but are not particularly limited to, an alkali metal hydride, an alkali metal amide and a basic oxide. If such a compound is used, the proportion of a trans-isomer or a cis-isomer in the resultant isomers and the isomerization yield tend to be further improved. Of these, at least one selected from the group consisting of an alkali metal hydride and an alkali metal amide is preferable. Examples of the alkali metal hydride include, but are not particularly limited to, sodium hydride, potassium hydride, lithium hydride, lithium aluminum hydride and sodium boron hydride. Examples of the alkali metal amide include, but are not particularly limited to, sodium amide, potassium amide, lithium amide, lithium diisopropylamide and sodium bis (trimethylsilyl)amide. Examples of the basic oxide include, but are not particularly limited to, lithium oxide, sodium oxide, potassium oxide, cesium oxide, magnesium oxide, calcium oxide, strontium oxide and barium oxide.

Examples of the alkaline earth metal include, but are not particularly limited to, metallic magnesium and metallic calcium.

Examples of the alkaline earth metal-containing compound include, but are not particularly limited to, an alkaline earth metal hydride. Examples of the alkaline earth metal hydride include, but are not particularly limited to, calcium hydride and magnesium hydride.

Of the above compounds, at least one selected from the group consisting of metallic sodium, a sodium amide and sodium hydride is particularly preferable. If such a compound is used, the proportion of a trans-isomer or a cis-isomer in the resultant isomers obtained and the isomerization yield tend to be further improved.

The amount of the alkali metal used herein relative to one mole of a benzylamine compound is preferably 0.10 to 10 mol equivalents and more preferably 1 to 4 mol equivalents. If the amount of the alkali metal used herein falls within the above range, the isomerization reaction tends to more efficiently proceed.

The isomers and an isomer mixture of a bis(aminomethyl) cyclohexane obtained by the isomerization method of the embodiment can be isolated by a method usually employed such as distillation.

In the isomerization method of the embodiment, if 1,4-bis(aminomethyl)cyclohexane is used as a bis(aminomethyl) cyclohexane, the content of a trans-isomer in the resultant product is preferably 77% or more, and more preferably 80% or more. Note that, the symbol "%" used herein refers to mol %.

In the isomerization method of the embodiment, if 1,3-bis(aminomethyl)cyclohexane is used as a bis(aminomethyl) cyclohexane, the content of a cis-isomer in the resultant product is preferably 80% or more. Note that, the symbol "%" used herein refers to mol %.

EXAMPLES

Now, the present invention will be more specifically described by way of Examples and Comparative Examples. However, the present invention is not limited to these Examples.

[Isomer Composition]

The isomer composition (cis/trans ratio) was analyzed by use of gas chromatography equipment equipped with a capillary column, CP-Volamine, manufactured by Valian.

Since the trans-isomer of 1,4-bis(aminomethyl)cyclohexane has a lower boiling point than the cis-isomer, the isomer first detected by gas chromatography is the trans-isomer and the isomer detected later is the cis-isomer. Since the cis-isomer of 1,3-bis(aminomethyl)cyclohexane has a lower boiling point than the trans-isomer, the isomer first detected by gas chromatography is the cis-isomer and the isomer detected later is the trans-isomer. The proportion of a trans-isomer was calculated in accordance with the expression:

Area value of a trans-isomer/(area value of cis-isomer+ area value of a trans-isomer)×100, and the proportion of a cis-isomer was calculated in accordance with the expression:

100−trans-isomer ratio.

[Recovery Rate]

The recovery rate was calculated from the weight of the bis(aminomethyl)cyclohexane, which was obtained by the internal standard method of the above gas chromatographic analysis, in accordance with the following expression:

Recovery rate (%)=(weight of bis(aminomethyl)cyclohexane in reaction solution)/(weight of starting bis(aminomethyl)cyclohexane)×100.

[Starting Material]

As the benzylamine compound and alkali metal-containing compound, those available as reagents were used. As 1,4-bis(aminomethyl)cyclohexane having an isomer composition (cis/trans ratio) of 60/40, para-xylylenediamine was nuclear-hydrogenated in the presence of a catalyst, Ru-alumina, in accordance with a technique known in the art (for example, a method disclosed in Japanese Patent Laid-Open No. 50-126638) and further purified by distillation and then put in use.

Example 1

In a 500 ml-flask, 200 g of 1,4-bis(aminomethyl)cyclohexane (cis/trans=60/40), 8.0 g of 4-methylbenzylamine (4-MBA) and sodium amide (2.9 g) were added. A pipe made of SUS316 and having a diameter of 3 mmϕ was inserted in the solution in the flask. While continuously injecting argon through the pipe at a flow rate of 200 mL/min, an isomerization reaction was carried out at 120° C. for 5 hours. The isomer composition (cis/trans) obtained after the isomerization reaction was 18/82 and the recovery rate of the 1,4-bis(aminomethyl)cyclohexane was 89%. The time-dependent change of the trans-isomer proportion is shown in FIG. 1.

Example 2

In a 500 ml-flask, 200 g of 1,4-bis(aminomethyl)cyclohexane (cis/trans=60/40), 9.0 g of meta-xylylenediamine and sodium amide (2.9 g) were added. A pipe made of SUS316 and having a diameter of 3 mmϕ was inserted in the solution in the flask. While continuously injecting argon through the pipe at a flow rate of 200 mL/min, an isomerization reaction was carried out at 120° C. for 5 hours. The isomer composition (cis/trans) obtained after the isomerization reaction was 17/83 and the recovery rate of the 1,4-bis (aminomethyl)cyclohexane was 87%.

Example 3

In a 500 ml-flask, 200 g of 1,4-bis(aminomethyl)cyclohexane (cis/trans=60/40), 7.1 g of benzylamine and sodium amide (2.9 g) were added. A pipe made of SUS316 and having a diameter of 3 mmϕ was inserted in the solution in the flask. While continuously injecting argon through the pipe at a flow rate of 200 mL/min, an isomerization reaction was carried out at 120° C. for 5 hours. The isomer composition (cis/trans) obtained after the isomerization reaction was 19/81 and the recovery rate of the 1,4-bis(aminomethyl)cyclohexane was 96%.

Example 4

In a 500 ml-flask, 200 g of 1,4-bis(aminomethyl)cyclohexane (cis/trans=60/40), 8.0 g of 4-methylbenzylamine (4-MBA) and sodium hydride (50-72%) (3.0 g) were added. A pipe made of SUS316 and having a diameter of 3 mmφ was inserted in the solution in the flask. While continuously injecting argon through the pipe at a flow rate of 200 mL/min, an isomerization reaction was carried out at 120° C. for 5 hours. The isomer composition (cis/trans) obtained after the isomerization reaction was 18/82 and the recovery rate of the 1,4-bis(aminomethyl)cyclohexane was 93%.

Comparative Example 1

In a 300-mL autoclave, 200 g of 1,4-bis(aminomethyl)cyclohexane (cis/trans=60/40), 8.0 g of 4-methylbenzylamine (4-MBA) and sodium amide (2.9 g) were added. An isomerization reaction was carried out at 120° C. for 5 hours while keeping the autoclave airtight. The isomer composition (cis/trans) obtained after the isomerization reaction was 29/71 and the recovery rate of the 1,4-bis(aminomethyl)cyclohexane was 92%. The time-dependent change of the trans-isomer proportion is shown in FIG. 1.

Comparative Example 2

In a 300-mL flask, 100 g of 1,4-bis(aminomethyl)cyclohexane (cis/trans=60/40), 4.0 g of 4-methylbenzylamine (4-MBA) and sodium amide (1.4 g) were added and an isomerization reaction was carried out under an argon atmosphere at 120° C. for 5 hours. The isomer composition (cis/trans) obtained after the isomerization reaction was 24/76 and the recovery rate of the 1,4-bis(aminomethyl)cyclohexane was 90%. The time-dependent change of the trans-isomer proportion is shown in FIG. 1.

Comparative Example 3

In a 500-mL flask, 200 g of 1,4-bis(aminomethyl)cyclohexane (cis/trans=60/40), 9.0 g of meta-xylylenediamine and sodium amide (2.9 g) were added and an isomerization reaction was carried out under an argon atmosphere at 120° C. for 5 hours. The isomer composition (cis/trans) obtained after the isomerization reaction was 44/56 and the recovery rate of the 1,4-bis(aminomethyl)cyclohexane was 98%.

Comparative Example 4

In a 500-mL flask, 200 g of 1,4-bis(aminomethyl)cyclohexane (cis/trans=60/40), 7.1 g of benzylamine and sodium amide (2.9 g) were added and an isomerization reaction was carried out under an argon atmosphere at 120° C. for 5 hours. The isomer composition (cis/trans) obtained after the isomerization reaction was 31/69 and the recovery rate of the 1,4-bis(aminomethyl)cyclohexane was 93%.

Comparative Example 5

In a 500-mL flask, 200 g of 1,4-bis(aminomethyl)cyclohexane (cis/trans=60/40), 8.0 g of 4-methylbenzylamine (4-MBA) and sodium hydride (50-72%) (3.0 g) were added and an isomerization reaction was carried out under an argon atmosphere at 120° C. for 5 hours. The isomer composition (cis/trans) obtained after the isomerization reaction was 35/65 and the recovery rate of the 1,4-bis(aminomethyl)cyclohexane was 93%.

INDUSTRIAL APPLICABILITY

The present invention has industrial applicability as a method for isomerizing a bis(aminomethyl)cyclohexane useful as optical materials such as plastic lenses, prisms, optical fibers, information recording substrates and filters using e.g., a polyamide and a polyurethane.

The invention claimed is:

1. A method for isomerizing a bis(aminomethyl)cyclohexane, the method comprising isomerizing a bis(aminomethyl)cyclohexane while introducing an inert gas in a reaction solution comprising:
    a bis(aminomethyl)cyclohexane,
    at least one selected from the group consisting of an alkali metal, an alkali metal-containing compound, an alkaline earth metal and an alkaline earth metal-containing compound, and
    a benzylamine compound.
2. The method for isomerizing a bis(aminomethyl)cyclohexane according to claim 1, wherein the inert gas is at least one selected from the group consisting of helium, argon and nitrogen.
3. The method for isomerizing a bis(aminomethyl)cyclohexane according to claim 1, wherein the benzylamine compound is at least one selected from the group consisting of benzylamine, 3-methylbenzylamine, 4-methylbenzylamine, dibenzylamine, meta-xylylenediamine and para-xylylenediamine.
4. The method for isomerizing a bis(aminomethyl)cyclohexane according to claim 1, wherein the benzylamine compound is 4-methylbenzylamine.
5. The method for isomerizing a bis(aminomethyl)cyclohexane according to claim 1, wherein the reaction solution comprises an alkali metal-containing compound, which comprises sodium amide.
6. The method for isomerizing a bis(aminomethyl)cyclohexane according to claim 1, wherein an isomerization reaction temperature is 100 to 140° C.
7. The method for isomerizing a bis(aminomethyl)cyclohexane according to claim 1, wherein the introducing of the inert gas comprises bubbling.
8. The method for isomerizing a bis(aminomethyl)cyclohexane according to claim 1, wherein the bis(aminomethyl)cyclohexane is 1,4-bis(aminomethyl)cyclohexane.
9. The method for isomerizing a bis(aminomethyl)cyclohexane according to claim 1, wherein the bis(aminomethyl)cyclohexane is 1,3-bis(aminomethyl)cyclohexane.
10. The method for isomerizing a bis(aminomethyl)cyclohexane according to claim 8, wherein the 1,4-bis(aminomethyl)cyclohexane is obtained in a trans-isomer content of at least 77%.
11. The method for isomerizing a bis(aminomethyl)cyclohexane according to claim 9, wherein the 1,3-bis(aminomethyl)cyclohexane is obtained in a cis-isomer content of at least 80%.
12. The method for isomerizing a bis(aminomethyl)cyclohexane according to claim 1, wherein the method comprises isomerizing the bis(aminomethyl)cyclohexane while continuously introducing the inert gas in the reaction solution.

13. The method for isomerizing a bis(aminomethyl)cyclohexane according to claim 10, wherein the method comprises isomerizing the bis(aminomethyl)cyclohexane while continuously introducing the inert gas in the reaction solution.

14. The method for isomerizing a bis(aminomethyl)cyclohexane according to claim 11, wherein the method comprises isomerizing the bis(aminomethyl)cyclohexane while continuously introducing the inert gas in the reaction solution.

15. The method for isomerizing a bis(aminomethyl)cyclohexane according to claim 12, wherein:
the inert gas is at least one selected from the group consisting of helium, argon and nitrogen;
the benzylamine compound is at least one selected from the group consisting of benzylamine, 3-methylbenzylamine, 4-methylbenzylamine, dibenzylamine, meta-xylylenediamine and para-xylylenediamine;
the reaction solution comprises at least one of metallic sodium, sodium amide, and sodium hydride; and
an amount of the benzylamine compound relative to one mole of the bis(aminomethyl)cyclohexane is 0.001 to 0.10 mol equivalents.

16. The method for isomerizing a bis(aminomethyl)cyclohexane according to claim 13, wherein:
the inert gas is at least one selected from the group consisting of helium, argon and nitrogen;
the benzylamine compound is at least one selected from the group consisting of benzylamine, 3-methylbenzylamine, 4-methylbenzylamine, dibenzylamine, meta-xylylenediamine and para-xylylenediamine;
the reaction solution comprises at least one of metallic sodium, sodium amide, and sodium hydride; and
an amount of the benzylamine compound relative to one mole of the bis(aminomethyl)cyclohexane is 0.001 to 0.10 mol equivalents.

17. The method for isomerizing a bis(aminomethyl)cyclohexane according to claim 14, wherein:
the inert gas is at least one selected from the group consisting of helium, argon and nitrogen;
the benzylamine compound is at least one selected from the group consisting of benzylamine, 3-methylbenzylamine, 4-methylbenzylamine, dibenzylamine, meta-xylylenediamine and para-xylylenediamine;
the reaction solution comprises at least one of metallic sodium, sodium amide, and sodium hydride; and
an amount of the benzylamine compound relative to one mole of the bis(aminomethyl)cyclohexane is 0.001 to 0.10 mol equivalents.

18. The method for isomerizing a bis(aminomethyl)cyclohexane according to claim 15, wherein the introducing of the inert gas comprises bubbling the inert gas in the reaction solution.

19. The method for isomerizing a bis(aminomethyl)cyclohexane according to claim 16, wherein the introducing of the inert gas comprises bubbling the inert gas in the reaction solution.

20. The method for isomerizing a bis(aminomethyl)cyclohexane according to claim 17, wherein the introducing of the inert gas comprises bubbling the inert gas in the reaction solution.

* * * * *